(12) United States Patent
Rea

(10) Patent No.: US 7,682,388 B2
(45) Date of Patent: Mar. 23, 2010

(54) STENT WITH LONGITUDINAL GROOVE

(75) Inventor: Susan Rea, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 267 days.

(21) Appl. No.: 11/668,991

(22) Filed: Jan. 30, 2007

(65) Prior Publication Data

US 2008/0183270 A1 Jul. 31, 2008

(51) Int. Cl.
*A61F 2/06* (2006.01)

(52) U.S. Cl. ...................... 623/1.42; 623/903

(58) Field of Classification Search ........ 623/1.15–1.48
See application file for complete search history.

(56) References Cited

U.S. PATENT DOCUMENTS

| | | | | |
|---|---|---|---|---|
| 6,071,305 | A * | 6/2000 | Brown et al. ............... | 623/1.43 |
| 6,273,913 | B1 * | 8/2001 | Wright et al. ............... | 623/1.42 |
| 6,287,628 | B1 * | 9/2001 | Hossainy et al. ............ | 427/2.3 |
| 6,379,381 | B1 * | 4/2002 | Hossainy et al. ........... | 623/1.42 |
| 6,395,326 | B1 * | 5/2002 | Castro et al. ............... | 427/2.24 |
| 7,326,238 | B1 * | 2/2008 | Kilpatrick et al. .......... | 623/1.13 |
| 7,357,813 | B2 * | 4/2008 | Burgermeister ............. | 623/1.17 |
| 7,402,173 | B2 * | 7/2008 | Scheuermann et al. ..... | 623/1.46 |
| 2002/0038145 | A1 * | 3/2002 | Jang ............................ | 623/1.15 |
| 2004/0117005 | A1 | 6/2004 | Nagarada et al. | |
| 2005/0209684 | A1 | 9/2005 | Alexander et al. | |
| 2005/0211680 | A1 | 9/2005 | Li et al. | |
| 2006/0147489 | A1 * | 7/2006 | Shanley et al. .............. | 424/425 |
| 2006/0228389 | A1 | 10/2006 | Li et al. | |

FOREIGN PATENT DOCUMENTS

| | | |
|---|---|---|
| EP | 001028672 | 6/2005 |
| WO | WO99/23977 A | 5/1999 |
| WO | WO03/047651 | 6/2003 |
| WO | WO2004/026182 | 4/2004 |
| WO | WO2004/026357 | 4/2004 |
| WO | WO2005/077305 | 8/2005 |
| WO | WO2006/105126 | 10/2006 |

OTHER PUBLICATIONS

Dalby, M. et al. "Interactions of Human Blood and Tissue Cell Types with 95-nm-High Nanotopography" IEEE Transactions on NanoBioscience, vol. 1, No. 1, Mar. 2002.
Wojciak-Stothard, et al. "Guidance and Activation of Murine Macrophages by NanoMetric Scale Topography," Experimental Cell Research 223, pp. 426-435 (1996), Article 0098.
Yim, E., et al. "Nanopattern-Induced Changes in Morphology and Motility of Smooth Muscle Cells," Biomaterials 26 (2005) 5405-5413.
Rea, S., et al., "Osteoblast-Like Cell Response to Bioactive Composites Surface-Topography and Composition Effects," www.interscience.wiley.com, Jun. 14, 2004.

* cited by examiner

*Primary Examiner*—Suzette J Gherbi

(57) ABSTRACT

A method of treating a vascular condition includes delivering a stent including at least one elongated axial slot to a target region of a vessel and receiving endothelial cell growth in the slots. A system for treating a vascular condition includes a catheter and a stent disposed on the catheter. The stent includes a stent framework including elongated axial slot formed therein and at least one therapeutic agent carried within the elongated axial slots. An outermost surface of the therapeutic agent is recessed within the elongated axial slots from the outer surface of the stent framework to allow endothelial cell growth within the elongated axial slots upon delivery of the stent to a target region of a vessel.

11 Claims, 5 Drawing Sheets

STENT WITH LONGITUDINAL GROOVE

TECHNICAL FIELD

This invention relates generally to medical devices for treating vascular conditions, and more particularly to a stent with a slot.

BACKGROUND OF THE INVENTION

Stents have become popular medical devices for treatment of vascular conditions. One difficulty with such devices is increasing the biocompatibility of the stent. Previously, this problem has been addressed by incorporating pharmaceutical ingredients and stent shape.

One attempt to help increase biocompatibility includes the use of a radial groove to encourage ingrowth of smooth muscle cells. However, such attempts do not address problems caused by tissues closer to the stent surface, such as the endothelial lining of vessel walls.

In an intact artery, the intima consists mainly of endothelial cells oriented longitudinally to provide good mechanical support and proper biologic function. When the vessel is injured and partially or completely denuded during stent deployment, the new endothelial layer that forms upon healing has a disordered, patchwork appearance that may undesirably affect both the mechanical and biological response capabilities of the vessel.

It would be desirable, therefore, to provide a stent that would overcome the limitations and disadvantages inherent in the devices described above.

SUMMARY OF THE INVENTION

A first aspect of the invention provides a method of treating a vascular condition that includes delivering a stent including at least one elongated axial slot to a target region of a vessel and receiving endothelial cell growth in the slots.

Another aspect of the invention provides a system for treating a vascular condition that includes a catheter and a stent disposed on the catheter. The stent includes a stent framework including at least one elongated axial slot formed therein and at least one therapeutic agent carried within the elongated axial slots. An outermost surface of the therapeutic agent is recessed within the elongated axial slots from the outer surface of the stent framework to allow endothelial cell growth within the elongated axial slots upon delivery of the stent to a target region of a vessel.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the drawings wherein like numbers refer to like structures.

Figure 1:
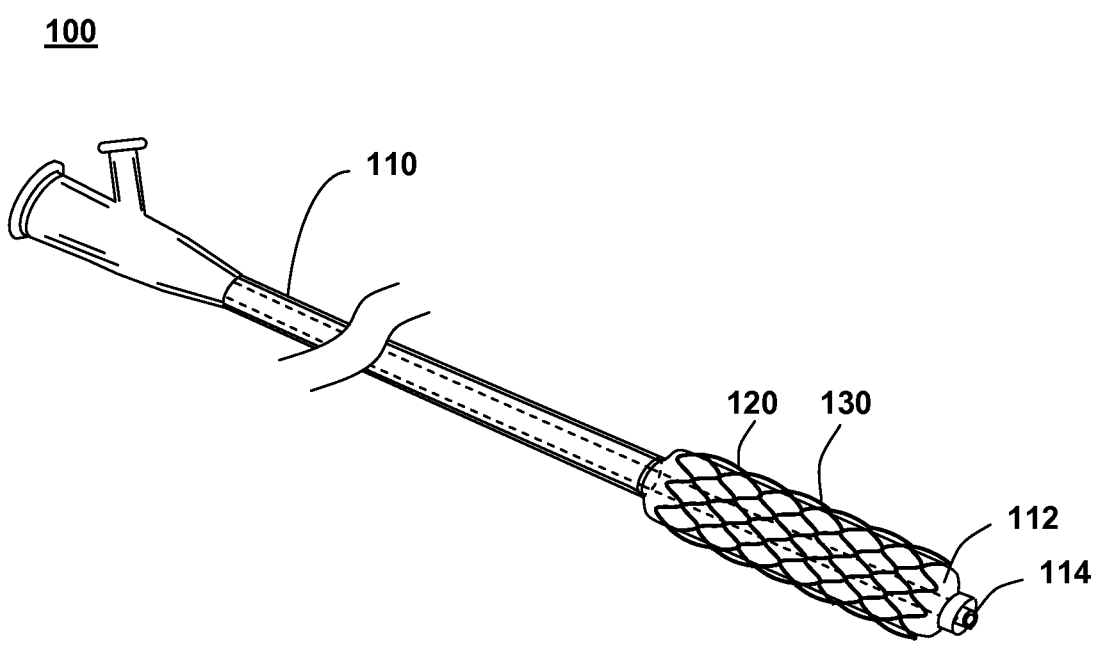
FIG. 1 is an illustration of a system for treating a vascular condition including a stent coupled to a catheter, in accordance with one embodiment of the current invention.

FIG. 1 shows an illustration of a system for treating a vascular condition, comprising a stent coupled to a catheter, in accordance with one embodiment of the present invention at 100. Stent with catheter 100 includes a stent 120 coupled to a delivery catheter 110. Stent 120 includes a stent framework 130 and, in some embodiments, a therapeutic agent 140 disposed on the stent framework 130. Therapeutic agent 140 includes at least a first therapeutic agent. In certain embodiments, therapeutic agent 140 includes at least two or more therapeutic agents.

Catheter-deployed stent 120 typically is used to treat vascular conditions, such as one or more blockages, occlusions, stenoses, or diseased regions in the coronary artery, femoral artery, peripheral arteries, and blood vessels in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

An exemplary therapeutic agent 140 includes or encapsulates one or more therapeutic agents. Therapeutic agent 140 may comprise one or more therapeutic agents dispersed within or encased by drug layers or barrier layers, such as an intermediate layer of magnesium, on stent 120, which are eluted or leached from stent 120 with, for example, controlled time delivery after deployment of stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Therapeutic agent 140 may comprise, for example, an antirestenotic agent such as rapamycin, a rapamycin derivative, or a rapamycin analog to prevent or reduce the recurrence of narrowing and blockage of the bodily vessel. Therapeutic agent 140 may comprise an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof. In one example, a first therapeutic agent comprises an antirestenotic drug such as rapamycin, a rapamycin derivative, or a rapamycin analog. The second therapeutic agent may comprise, for example, an anti-cancer drug such as camptothecin or other topoisomerase inhibitors. The therapeutic agent constituency in the drug layers may be, for example, between 0.1 percent and 50 percent of the drug layer by weight. In another example, the first therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammatant such as dexamethasone, and an optional second therapeutic agent such as 5-fluorouracil. In another embodiment, the therapeutic agent is one of a drug and a drug polymer.

In one example, a first therapeutic agent comprises an antirestenotic drug such as rapamycin, a rapamycin derivative, or a rapamycin analog. The second therapeutic agent may comprise, for example, an anti-cancer drug such as camptothecin or other topoisomerase inhibitors. The therapeutic agent constituency in the drug layers may be, for example, between 0.1 percent and 50 percent of the drug layer by weight. In another example, the first therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammation agent such as dexamethasone, and an optional second therapeutic agent such as 5-fluorouracil.

The elution rates of the therapeutic agents and total drug eluted into the body and the tissue bed surrounding the stent framework are based on the target thickness of therapeutic agent 140, the constituency and individual layer thicknesses of therapeutic agent 140, the nature and concentration of the therapeutic agents, the thickness and composition of any cap coat, and other factors. Therapeutic agent 140 may include and elute or leach multiple therapeutic agents to achieve the desired therapeutic effect. In some cases, a portion of a topcoat layer is absorbed into the body.

Catheter 110 of an exemplary embodiment of the present invention includes a balloon 112 that expands and deploys the stent within a vessel of the body. After positioning stent 120 within the vessel with the assistance of a guide wire traversing through a guidewire lumen 114 inside catheter 110, balloon 112 is inflated by pressurizing a fluid such as a contrast fluid or saline solution that fills a tube inside catheter 110 and balloon 112. Stent 120 is expanded until a desired diameter is reached, and then the fluid is removed, separating balloon 112 from stent 120 and leaving stent 120 deployed in the vessel of the body. Alternately, catheter 110 may include a sheath that retracts to allow expansion of a self-expanding version of stent 120.

Figure 2A:
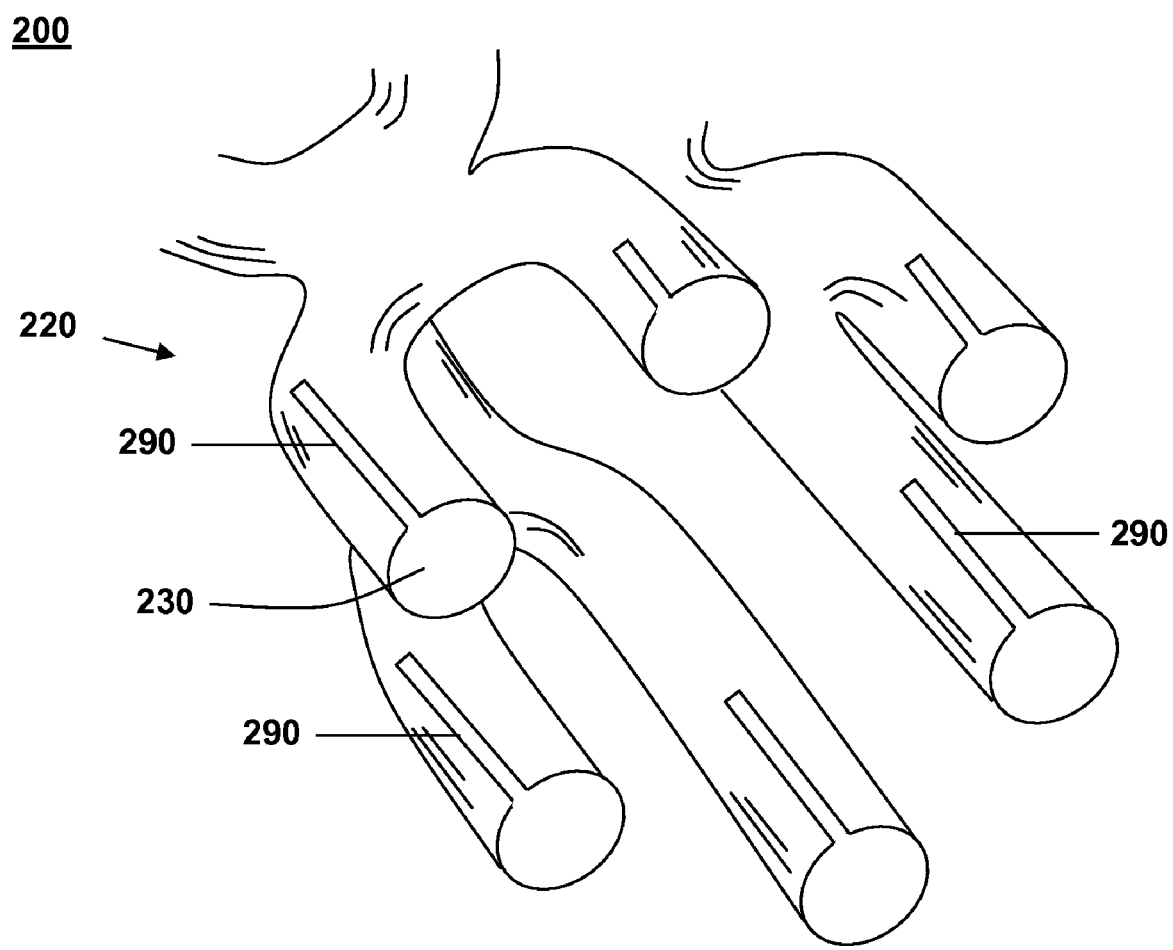
FIG. 2A is a cross-sectional perspective view of a stent, in accordance with one embodiment of the current invention.

FIG. 2A shows a cross-sectional perspective view of a stent, in accordance with one embodiment of the present invention at 200. Stent 220 includes a stent framework 230, in one embodiment with a drug coating disposed on stent framework 230. In certain embodiments, drug coating includes a plurality of thin drug layers.

Multiple sets of coating layers may be disposed on stent framework 230. For example, ten sets of layers, each layer on the order of 0.1 micrometers thick, can be alternately disposed on stent framework 230 to produce a two-micrometer thick coating. In another example, twenty sets of layers, each layer on the order of 0.5 micrometers thick, can be alternately disposed on stent framework 230 to produce a twenty-micrometer thick coating. The drug layers and the magnesium coating layers need not be the same thickness, and the thickness of each may be varied throughout drug coating 240. In one embodiment, the total quantity of magnesium is controlled to reduce potentially undesirable or toxic effects.

Stent framework 230 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art. In one example, the drug layers comprise a first therapeutic agent such as camptothecin, rapamycin, a rapamycin derivative, or a rapamycin analog.

In addition, stent framework 230 includes a plurality of elongated axial slots 290. Each of the elongated axial slots extends along a span of the stent framework 230 and defines a longitudinal slot axis substantially parallel with an axis defined by the body lumen. In one embodiment, the elongated slot axis is substantially parallel with the axis defined by the strut of the framework, depending on the geometric configuration of the stent framework. In another example, the elongated slot axis is substantially parallel with the axis defined by the lumen defined by the stent framework. Elongated axial slots 290, on deployment at a target site within a body lumen, will receive endothelial cell ingrowth. Within the same stent framework, different elongated axial slots 290 can assume different geometric configurations and different lengths. In addition, different therapeutic agents can be carried within distinct elongated axial slots 290 of the same stent framework. In one embodiment, the elongated axial slot grooves is oriented longitudinally after the stent is deployed. In one embodiment, the elongated axial slots are substantially 10-50 μm in width. In other embodiments, the elongated axial slots are substantially 1-15 μm in width, while in other embodiments, the elongated axial slots are substantially 45-100 μm in width. In one embodiment, the elongated axial slots are sized to be on the same scale as the endothelial cells.

Figure 2B:
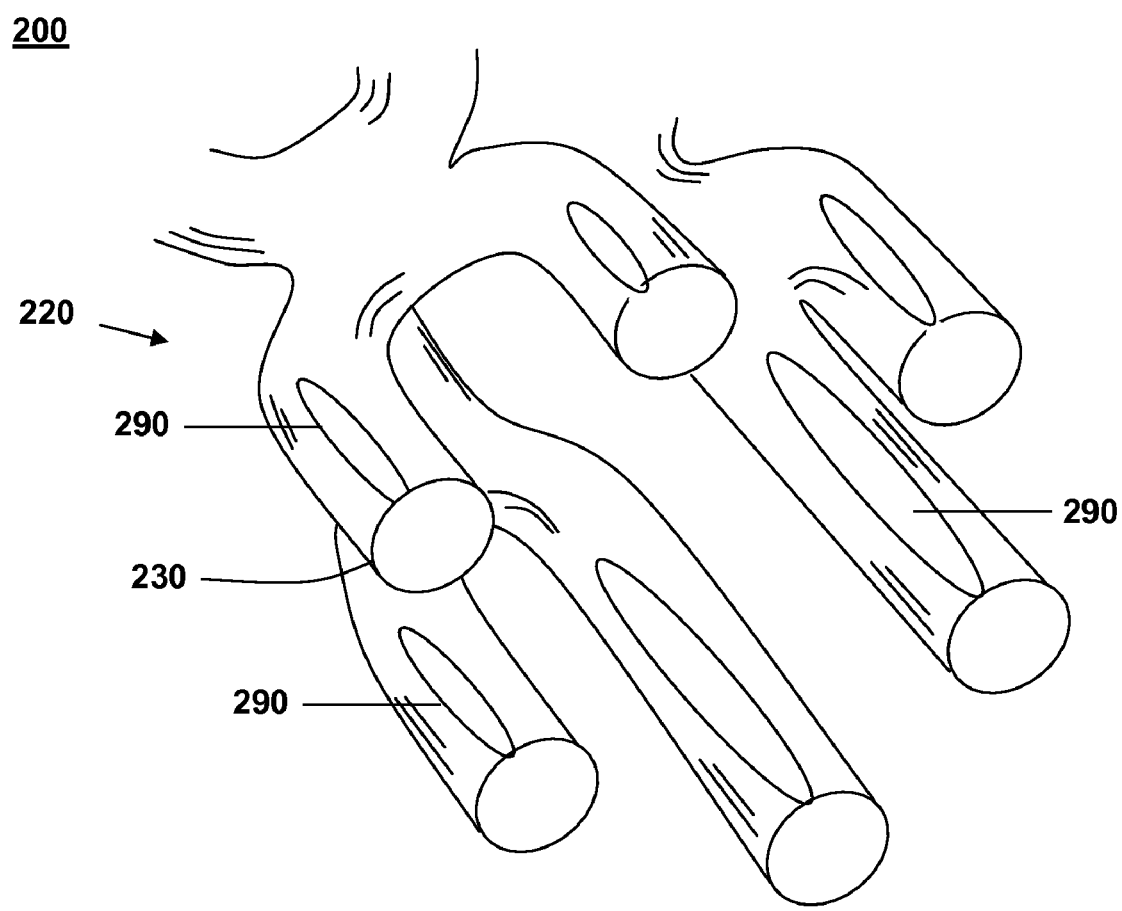
FIG. 2B is a cross-sectional perspective view of a stent, in accordance with one embodiment of the current invention

FIG. 2B illustrates another embodiment of a stent accordance with the invention. As illustrated in FIG. 2B, stent framework 230 includes elongated axial slots 290 including at least one radiused wall so that the elongated axial slot has a substantially ovoid geometric appearance.

Figure 3A:
FIGS. 3A, 3B, 3C, and 3D are illustrations of a cross section of an elongated axial slot, in accordance with one embodiment of the current invention.
Figure 3B:
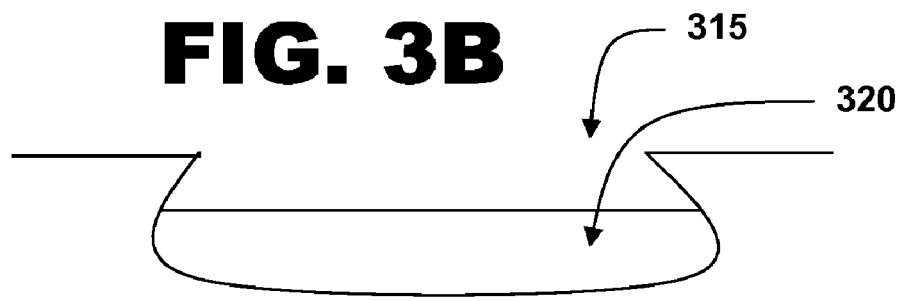
Figure 3C:
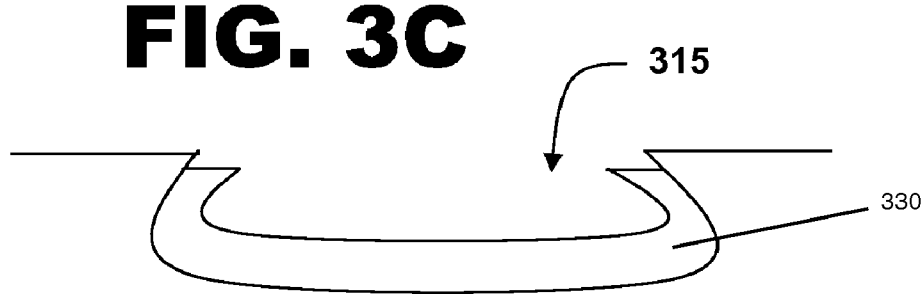
Figure 3D:
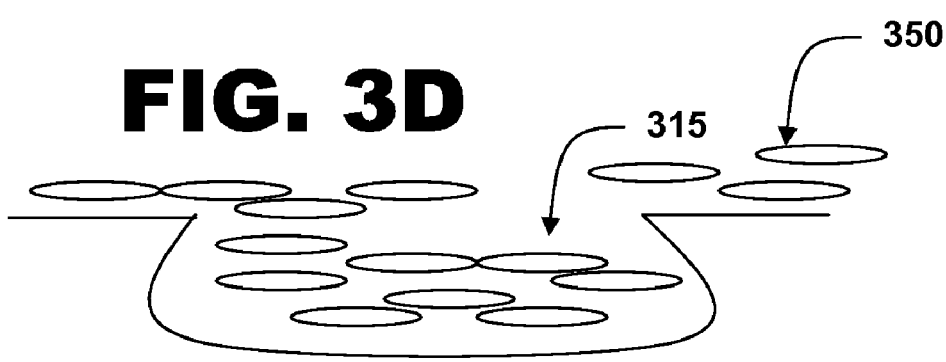

FIG. 3A illustrates a close up cross section of an elongated axial slot 315 of a stent framework 300 without the inclusion of any therapeutic agent. Although the elongated axial slot 315 includes a radius as illustrated in FIGS. 3A, 3B, and 3C, no such geometric limitation is anticipated, and the elongated axial slot can be any particular shape, including radiused and angled. FIG. 3B illustrates a cross section of a stent framework 301, with the elongated axial slot 315 only partially filled with a volume of therapeutic agent 320. Therapeutic agent 320 is illustrated as a pool of therapeutic agent, without significant shaping other than via the geometric shape of the elongated axial slot 315. FIG. 3C illustrates a cross section of a stent framework 302, with the elongated axial slot 315 only partially filled with a volume of therapeutic agent 330. In the embodiment illustrated in FIG. 3C, therapeutic agent 330 is shaped to assume a particular geometric pattern, such as with a forming tool. FIG. 3D illustrates a plurality of endothelial cells 350 received within elongated axial slot 315, such as after delivery to the target site within a vessel. As drawn, these cells are shown in cross-section and would have their longest axis running along the direction of the elongated axial slot 315. The cells and slot are not necessarily drawn to scale, as the relative size of the slot to the cells can be varied as desired for different applications as described previously.

The therapeutic agent is applied to the stent framework prior to delivery to a target region of a vessel, and elutes the therapeutic agent after delivery, in embodiments that include a therapeutic agent. The application of the therapeutic agent does not fill the entire volume of space defined by the elongated axial slot, in such embodiments, as seen in FIGS. 3B and 3C. The volume of therapeutic agent defines an outermost surface of the therapeutic agent recessed from the outer surface, or the exterior surface, of the stent framework.

Figure 4:
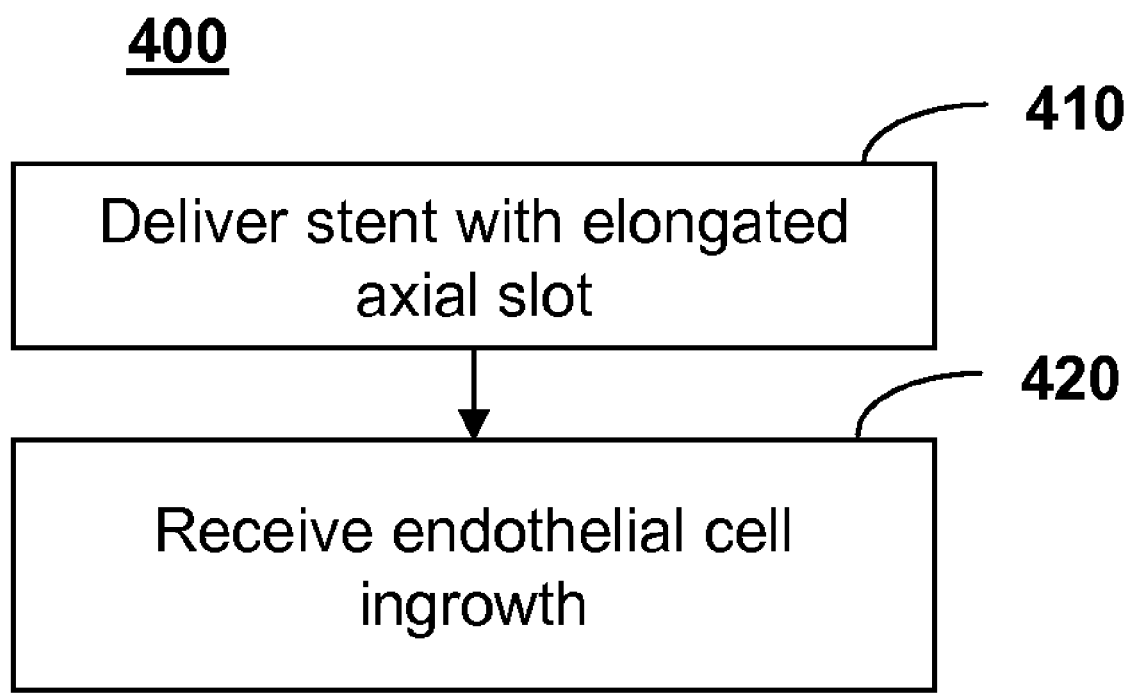
FIG. 4 is a flow diagram of a method treating a vascular condition, in accordance with one embodiment of the current invention.

FIG. 4 shows a flow diagram of a method of treating a vascular condition, in accordance with one embodiment of the present invention at 400.

A stent including at least one elongated axial slot is delivered to a target region of a vessel at step 410. The stent may be delivered using any appropriate technique, including, without limitation, a catheter.

The elongated axial slot receives endothelial cell growth at step 420. Endothelial cell growth is encouraged by the axial orientation of the elongated axial slot so that the orientation of the slot naturally lines up with the natural orientation of the endothelial cells within the vessel.

In one embodiment, an electric field is applied to the stent to further assist in angiogenesis. The electric field, in one embodiment, is limited to the approximate field generated by a skin wound.

While the invention has been described with reference to particular embodiments, it will be understood by one skilled in the art that variations and modifications may be made in form and detail without departing from the spirit and scope of the invention.

What is claimed is:

1. A method of treating a vascular condition, the method comprising:
   delivering a stent including at least one elongated axial slot to a target region of a vessel, wherein the at least one elongated axial slot prior to delivery is partially filled with at least one therapeutic agent such that an outermost surface of the therapeutic agent is recessed from an outer surface of the stent such that a gap is formed between the outermost surface of the therapeutic agent and the outer surface of the stent;
   expanding the stent into contact with a vessel wall of the vessel;
   orienting the at least one elongated axial slot of the expanded stent parallel to a longitudinal axis of the vessel; and
   receiving endothelial cell growth in the slots after the stent is expanded into contact with the vessel wall.

2. The method of claim 1 further comprising:
   eluting the at least one therapeutic agent after delivery.

3. The method of claim 1 wherein the therapeutic agent comprises one of a drug and a drug polymer.

4. A system for treating a vascular condition, comprising:
   a catheter;
   a stent disposed on the catheter, the stent including a stent framework including at least one elongated axial slot formed therein, wherein the at least one elongated axial slot is formed in the stent framework such that the at least one elongated axial slot is oriented longitudinally along an axis of a target region of a vessel when the stent is deployed; and
   at least one therapeutic agent carried within the at least one elongated axial slot, wherein an outermost surface of the therapeutic agent is recessed within the at least one elongated axial slot from the outer surface of the stent framework such that a gap is formed between the outermost surface of the therapeutic agent and the outer surface of the stent to allow endothelial cell growth from the vessel within the at least one elongated axial slot upon delivery of the stent to the target region of the vessel.

5. The system of claim 4 wherein the therapeutic agent comprises one of a drug and a drug polymer.

6. The system of claim 4 wherein the at least one elongated axial slot has a width of 45 to 100 μm.

7. The system of claim 4 wherein the at least one elongated axial slot has a width of 1 to 15 μm.

8. The system of claim 4 wherein the at least one elongated axial slot has a width of 5 to 30 μm.

9. The method of claim 1 wherein the at least one elongated axial slot has a width of 45 to 100 μm.

10. The method of claim 1 wherein the at least one elongated axial slot has a width of 1 to 15 μm.

11. The method of claim 1 wherein the at least one elongated axial slot has a width of 5 to 30 μm.

* * * * *